(12) United States Patent
Bates

(10) Patent No.: US 10,186,341 B2
(45) Date of Patent: Jan. 22, 2019

(54) X-RAY SOURCE

(71) Applicant: David Alan Bates, East Sussex (GB)

(72) Inventor: David Alan Bates, East Sussex (GB)

(73) Assignee: Torr Scientific Ltd., East Sussex (GB)

( * ) Notice: Subject to any disclaimer, the term of this patent is extended or adjusted under 35 U.S.C. 154(b) by 0 days.

(21) Appl. No.: 14/893,911

(22) PCT Filed: May 21, 2014

(86) PCT No.: PCT/GB2014/051545
§ 371 (c)(1),
(2) Date: Nov. 24, 2015

(87) PCT Pub. No.: WO2014/188176
PCT Pub. Date: Nov. 27, 2014

(65) Prior Publication Data
US 2016/0111177 A1   Apr. 21, 2016

(30) Foreign Application Priority Data
May 24, 2013  (GB) .................................. 1309403.2

(51) Int. Cl.
*G21K 1/06* (2006.01)
*H01J 35/02* (2006.01)
(Continued)

(52) U.S. Cl.
CPC ......... *G21K 1/067* (2013.01); *G01N 23/2273* (2013.01); *G21K 1/06* (2013.01);
(Continued)

(58) Field of Classification Search
CPC ............... G21K 1/06; G21K 2201/062; G21K 2201/064; G21K 1/062; G21K 2201/067;
(Continued)

(56) References Cited

U.S. PATENT DOCUMENTS

| | | | | |
|---|---|---|---|---|
| 2002/0064253 A1* | 5/2002 | Gutman | ................... | G21K 1/06 378/84 |
| 2011/0170666 A1* | 7/2011 | Chen | .................... | G01N 23/223 378/84 |
| 2013/0016813 A1* | 1/2013 | Yamazui | ............ | G01N 23/2273 378/64 |

FOREIGN PATENT DOCUMENTS

| | | |
|---|---|---|
| JP | H0618700 | 1/1994 |
| JP | 2002048738 | 2/2002 |

(Continued)

*Primary Examiner* — Hoon K Song
(74) *Attorney, Agent, or Firm* — Rutan & Tucker, LLP; Hani Z. Sayed

(57) ABSTRACT

An X-ray source comprising:
  an elongate tubular housing adapted to be fitted into a port of and extend into a chamber containing a sample to be analyzed, said housing containing:
    an electron gun and a target mounted in the housing, the electron gun being arranged to direct electrons to a point on the target such that the target radiates X-rays; and
    a monochromator arranged to focus X-rays radiated from the target to a focal point on a sample in the chamber;
  wherein the monochromator is positioned, and comprises a material selected such that the target, the monochromator and the focal point on the sample are substantially in-line within the envelope of the tubular housing.

13 Claims, 18 Drawing Sheets

(51) Int. Cl.
*H05G 1/02* (2006.01)
*G01N 23/2273* (2018.01)

(52) U.S. Cl.
CPC ............... *H01J 35/02* (2013.01); *H05G 1/02* (2013.01); *G21K 2201/062* (2013.01); *G21K 2201/064* (2013.01); *H01J 2235/163* (2013.01)

(58) Field of Classification Search
CPC .... G21K 2201/061; G21K 1/02; G21K 1/065; G21K 1/00
See application file for complete search history.

(56) References Cited

FOREIGN PATENT DOCUMENTS

| | | |
|---|---|---|
| JP | 20080268105 | 11/2008 |
| WO | WO 2009111454 | 9/2009 |

\* cited by examiner

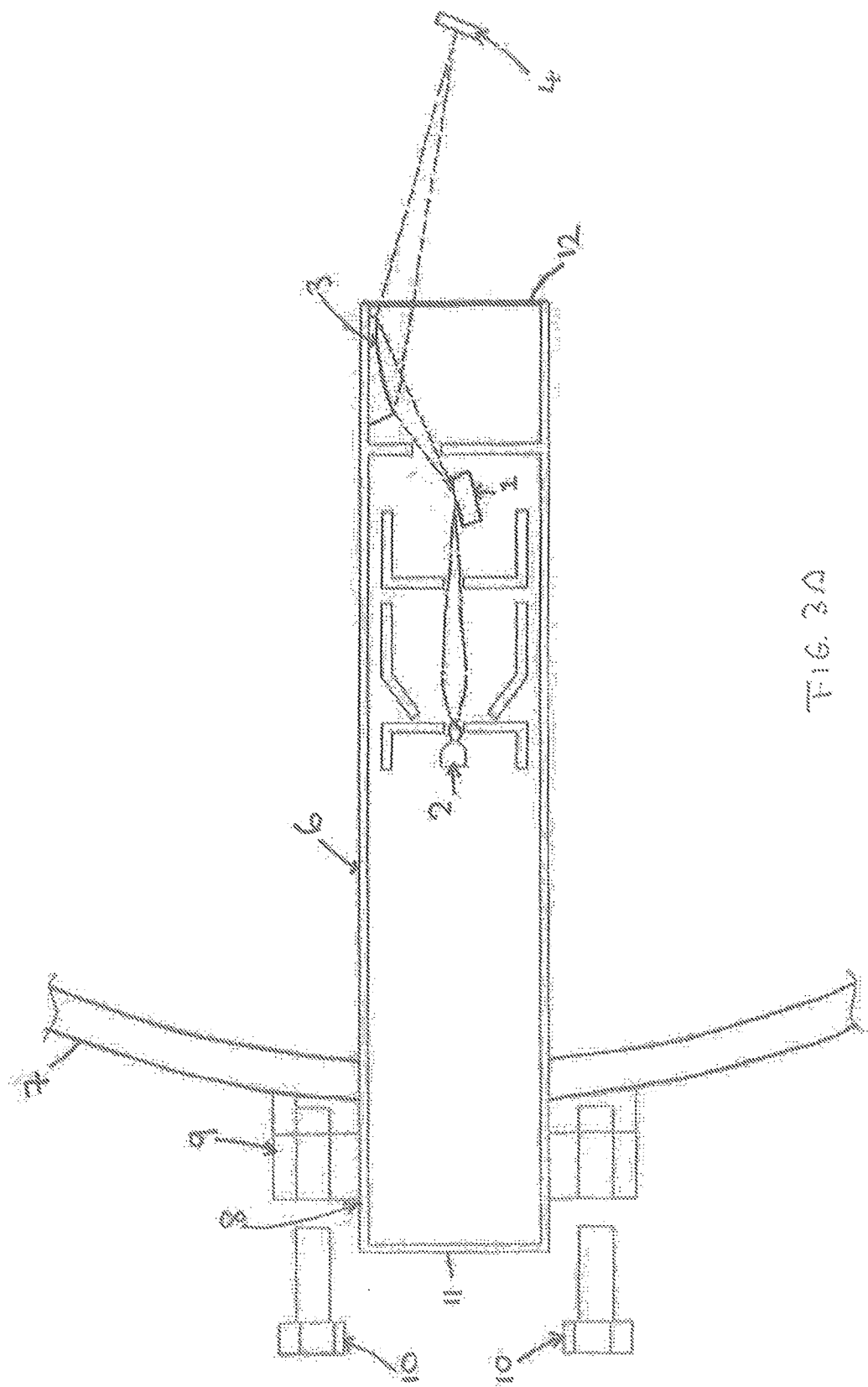

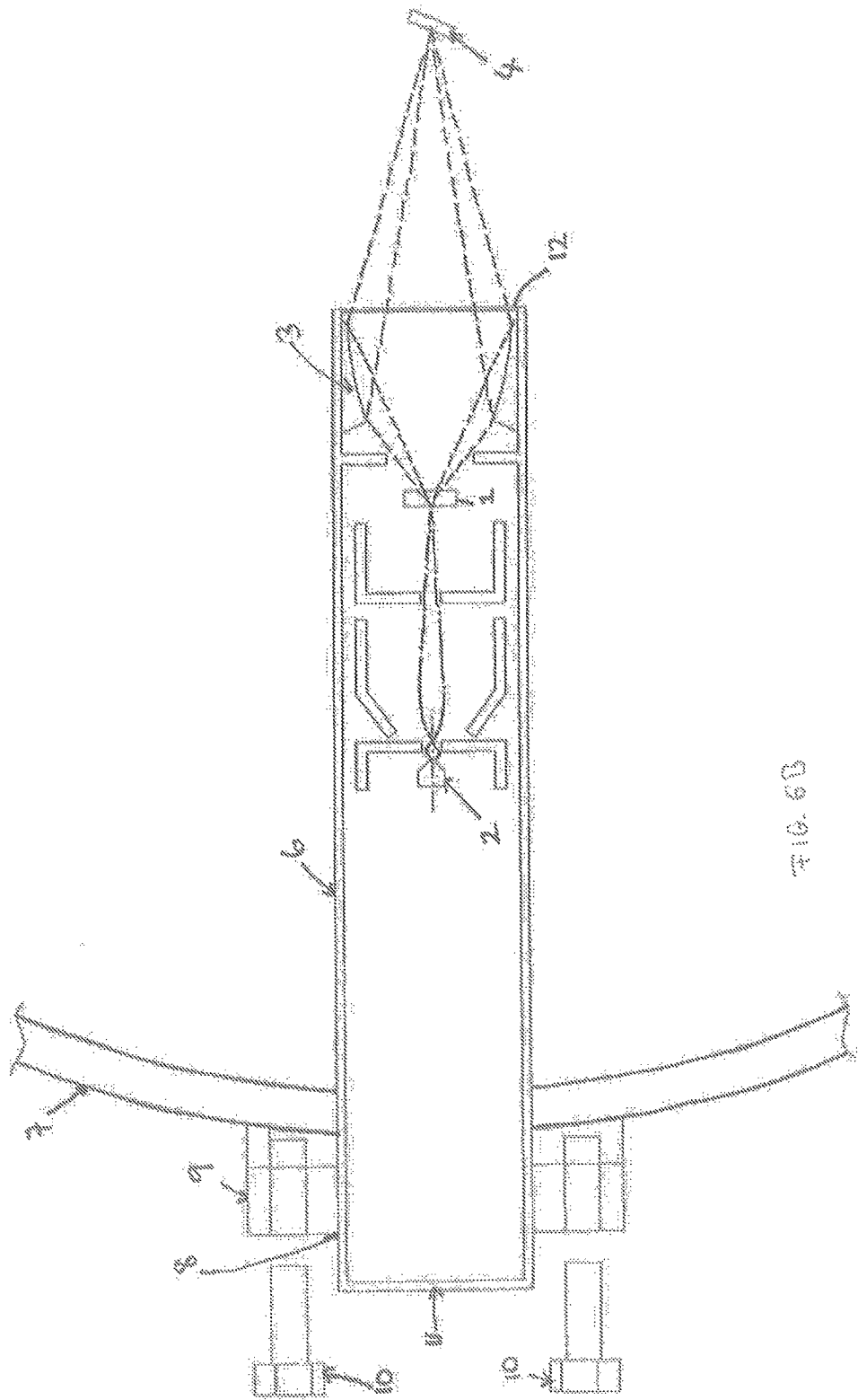

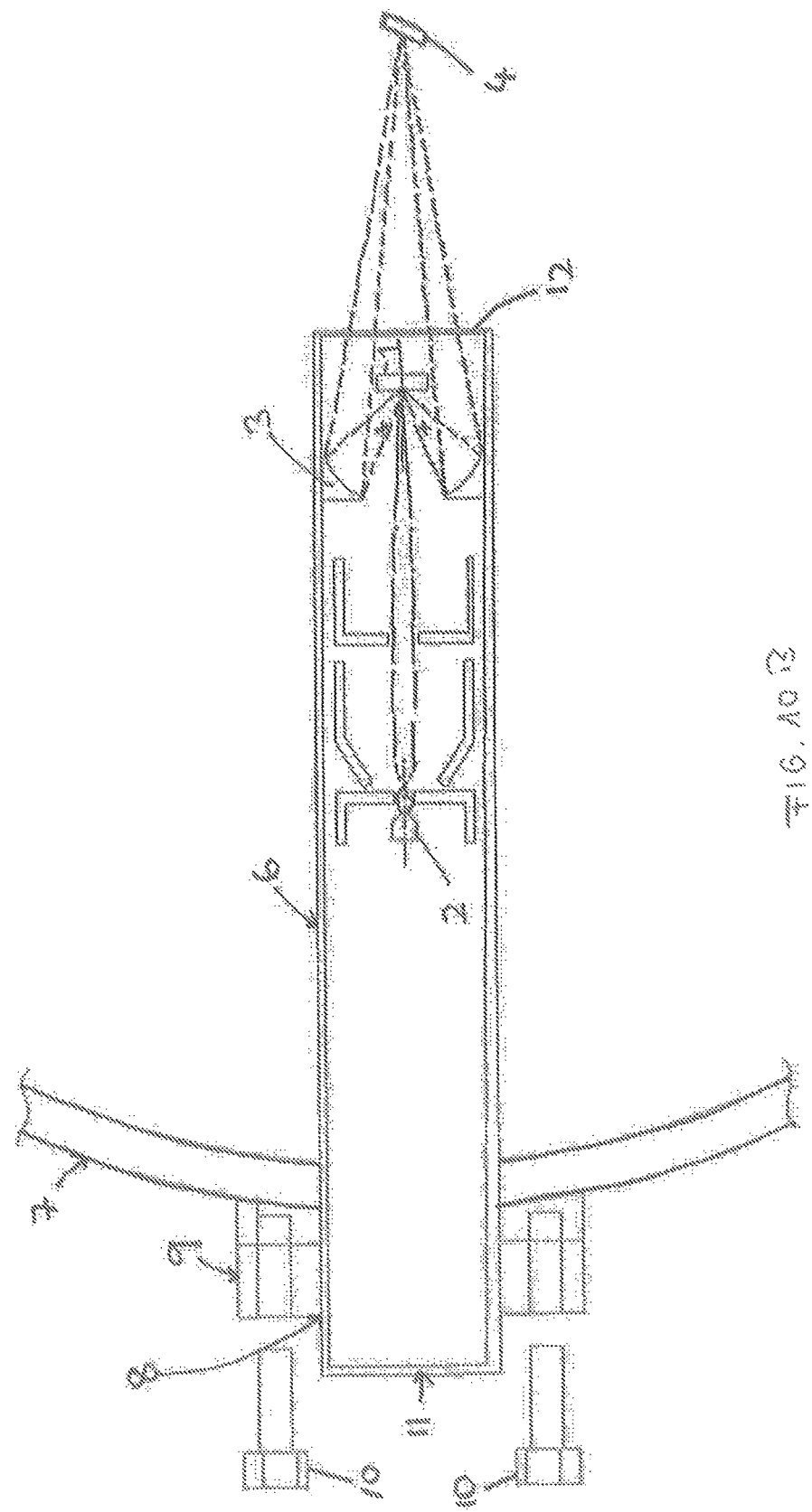

X-RAY SOURCE

The present invention is concerned with providing an X-ray source for producing X-rays for, for example, analysis of a sample. Specifically, the invention is a source of X-rays for X-ray photoelectron spectroscopy (XPS) but could, conceivably, find use in any application where a fairly narrow range of X-ray wavelengths is required.

X-rays are produced as electrons give up energy, provided the energy is surrendered in large enough quantities. Typically, this can be achieved by rapidly decelerating moving electrons, or by allowing an atomic electron to move to a position sufficiently closer to the atomic nucleus.

X-ray photoelectron spectroscopy (XPS) is a surface analysis technique of a sample that uses X-rays to eject electrons from atoms in the top few nm of the sample surface. The binding energy of an ejected electron can be deduced if the energy of the ejecting X-ray photon is known. The binding energy of the electron is characteristic of the element from which it came, so XPS can be used to identify the elements present in the surface of the sample. Subtle differences in the binding energy, smaller than the differences between different elements, can provide information on the chemical environment of the atom.

An XPS X-ray source uses accelerated electrons to excite or eject electrons from within a 'target' material, typically aluminium or magnesium. X-rays are produced when the electrons strike the target, but these are broad spectrum and yield less than precise information in the analysis. Electrons ejected from the atoms of the target material are replaced by electrons further from the nucleus—it is this that produces X-rays at a number of discrete wavelengths, or 'lines', that are characteristic of the target material. One of these lines will be used for the analyses.

In order to extract the maximum information from the sample, the X-rays should have as narrow a range of wavelengths as possible. The X-ray source on some XPS systems provides monochromated X-rays, such that the wavelength—and therefore the energy—of the photons delivered to the sample is tightly constrained. Monochromated sources provide a better signal-to-noise ratio and better energy resolution then non-monochromated sources. In addition, the X-rays in a monochromated system can be focussed to a small spot on the sample, allowing spatially-resolved analyses. Typically, a disadvantage of small-spot XPS is low X-ray flux. In part this is due to the monochromating process, by definition, selecting against and suppressing wavelengths that are not required. There is also a difficulty in dissipating heat produced at the site of small-spot X-ray generation (more later). The higher the X-ray flux, the less analysis time is needed to separate signal from noise.

A typical X-ray source and monochromator generally comprises an electron gun, a target and a monochromating crystal.

An electron gun produces electrons with sufficient velocity to produce the required X-rays from the target material. This must happen in a vacuum as electrons would collide with air molecules and fail to reach the target. For small spot XPS, the electrons are often focussed onto a small spot on the target. Heat generated by the electrons within this spot is liable to damage the target material, and cooling systems are preferably used to prevent this from happening. Dissipation of this heat remains a major technical obstacle to producing a large X-ray flux in a small-spot XPS system.

The target is the material that generates the X-rays when struck by electrons from the gun. It is typically (but not exclusively) a metallic coating of several μm thickness on a copper anode assembly. The copper of the anode assembly may be water cooled, and the region of the target that bears the electron impact may be coated directly onto diamond, which conducts heat several times better than copper.

X-rays are generated from the target material in all directions. A proportion of these will arrive at the monochromating crystal, where the narrow wavelength band of interest is selectively focussed onto the sample for analysis. The solid angle that the collecting face of the crystal subtends at the target is proportional to the X-ray flux delivered at the sample.

A detector analyses the signal from the impacting X-rays.

The monochromator crystal makes use of a phenomenon known as Bragg diffraction to selectively focus X-rays onto the sample. For this reason, the crystal is commonly called a Bragg crystal. For any chosen wavelength, only X-rays that strike the crystal atomic lattice structure at a particular angle are 'reflected'. This angle is dictated by the atomic spacing within the crystal, and therefore varies according to which crystal material is used. X-rays of the chosen wavelength arriving at the correct Bragg angle experience constructive interference and are diffracted back as if reflected; X-rays of the chosen wavelength arriving at other than the Bragg angle, or X-rays that arrive at that Bragg angle but with a different wavelength, interfere destructively and are not diffracted.

To focus the monochromated X-rays onto the sample, a system known as Johansson geometry is employed, involving an imaginary circle known as a Rowland circle.

A Rowland Circle is an imaginary circle with the target, Bragg crystal and sample arranged around the perimeter of the circle. The crystal surface is ground to the radius of the Rowland circle, but only after the lattice planes of the crystal have been bent such that all incoming X-ray photons from the target strike the lattice planes with the same angle of incidence and those of the desired wavelength are focussed onto the sample. The angle of incidence and the lattice spacing of the crystal are chosen to select, according to Bragg's law, the wavelength of interest.

In the example shown in FIG. 1, the X-ray source (target) 1 and sample 4 are at opposite ends of the horizontal diameter, 9 and 3 on a clock face, with the Bragg crystal 3 at the 12 o'clock position. The crystal surface is ground to the radius of the Rowland circle, R, while the planes of the crystal are bent to a radius of approximately 2R, i.e. their centre of curvature is at the bottom point of the circle (6 o'clock).

Bragg crystals are toroidal: there are two superimposed curvatures. They have curvature that matches the Rowland circle in the plane of the page, but they also have curvature through the plane of the page.

The Rowland circle also protrudes in 3D out of the page, forming a shape described by rotation about an imaginary line joining the target and the sample. In the above case a sphere would result as the centre of rotation is the diameter. If this line were not a diameter the 3D shape could be more like a rugby ball or a ring doughnut. These are all examples of toroids—shapes that exhibit two coexisting curvatures, here at 90° to each other.

In the configuration of FIG. 1, the angle that the path of the incoming photon makes with the lattice plane is around 45°, a convenient angle for illustration. In commercial XPS systems the crystal is generally quartz, giving a Bragg angle of around 79°.

X-ray source/monochromator apparatus currently commercially available are based around such a quartz Bragg (monochromating) crystal technology, and for this reason are constrained to a particular geometry. This necessitates that the apparatus has a certain geometry and that it is mounted external to the vacuum chamber.

This steep angle means that quartz-based monochromators by necessity have a tall aspect ratio (to give sufficient 'working distance'—the distance from target/crystal to sample). Most systems will need a minimum working distance of 25 mm or so. The tall aspect of the monochromator as can be seen in the example schematic view of FIG. 2, along with the numerous bolt-ons that require a line of sight to the sample. Part of the reason that the system has such tall aspect ratio is that quartz is the crystal used, and the angle that the most popular X-ray wavelength (that of aluminium) makes with quartz is ~79° C., so to give enough distance from X-ray source to sample such that the X-ray source is outside the main chamber, the crystal housing must be a considerable height above the port on the chamber.

The disadvantages of such configurations include that it is bulky and protrudes out from chamber. Other instruments may require access to the sample and, with space around the vacuum chamber being limited, a tall, bulky system can interfere with the positioning of these instruments. Also, the space inside the monochromator must be held in vacuum, and having extra volume to evacuate adds to pumping demands. The system also has a poor solid angle of X-ray capture at the crystal, as the solid angle of X-ray capture decreases with the square of distance from target to crystal. Further, the extra material requirements for such a system can add substantially to the overall cost.

The present invention aims to overcome these advantages by providing a monochromating X-ray source that has a substantially linear configuration that will fit substantially within the vacuum chamber.

Accordingly, the present invention provides an X-ray source comprising:

an elongate tubular housing adapted to be fitted into a port of and extend into a chamber containing a sample to be analysed, said housing containing:

an electron gun and a target mounted in the housing, the electron gun being arranged to direct electrons to a point on the target such that the target radiates X-rays; and a monochromator arranged to focus X-rays radiated from the target to a focal point on a sample in the chamber;

wherein the tubular housing has an inner diameter (D) and a central axis along its length, and wherein the monochromator is positioned, and comprises a material selected such that the focal point of the X-rays on the sample lies at a radial distance from the central axis not greater than the radius (D/2) of the housing, and wherein the point on the target is also at a radial distance from the central axis not greater than the radius of the housing, such that the target, the monochromator and the focal point on the sample are all contained within a radial area not greater than the diameter of the housing.

Preferably, the apparatus will be contained in a tubular outer housing that can be mounted, preferably using existing flange-mountings, to a port of the vacuum chamber and will extend through the port into the chamber.

In one embodiment, the tubular housing has a central axis along its length, and wherein the point on the target is positioned on the central axis, and wherein the monochromator is positioned and comprises a material selected such that the focal point of the X-rays on the sample also lies on the central axis. It is not, however, essential that the respective points lie on the centreline of the housing, so long as they lie within the envelope defined by the tubular housing.

In one commercial embodiment the housing diameter is less than 38 mm; in another, less than 35 mm.

The target may be a planar target arranged with a surface to receive electrons from the electron gun and to radiate X-rays towards the monochromator.

Alternatively, the target may be arranged to receive electrons at a first surface and to radiate X-rays from a second, opposite surface, where either the electrons or the X-rays pass through the body of the target from the first surface to the second surface.

The target is preferably a target-body comprising e.g. a diamond and/or copper substrate, and a metallic coating comprising e.g. aluminium.

Preferably, the target is cooled, e.g. by a system of circulating liquid. This may improve heat dissipation.

According to another aspect of the invention, there is provided an apparatus for X-ray analysis of a sample, comprising an X-ray source as defined above, a vacuum chamber comprising a port to which the housing of the X-ray source is mounted such that the X-ray source extends through the port into the vacuum chamber, wherein the sample to be analysed is, in use, located at the focal point of the X-rays from the monochromator.

The monochromator is preferably a diffracting crystal, preferably a Bragg crystal. Preferably a material other than quartz is used, e.g. a mica crystal such as muscovite.

In preferred embodiments, the crystal, or crystal segments are provided on or close to the inner surface of the tubular housing, extending at least part way around the inner surface. In one embodiment, the crystal, either as a single piece or as a series of segments and spaces between segments extends substantially right around, i.e. 360°, the inner surface of the housing. Of course smaller ranges also work.

Preferred embodiments of the invention will now be described, with reference to the drawings.

FIGS. 3A, B and C show, respectively, a cross-sectional schematic view, a ray diagram and a Rowland circle view for one embodiment of the invention.

FIGS. 4A-4D show the X-ray paths of an embodiment of the invention.

Figure 5:
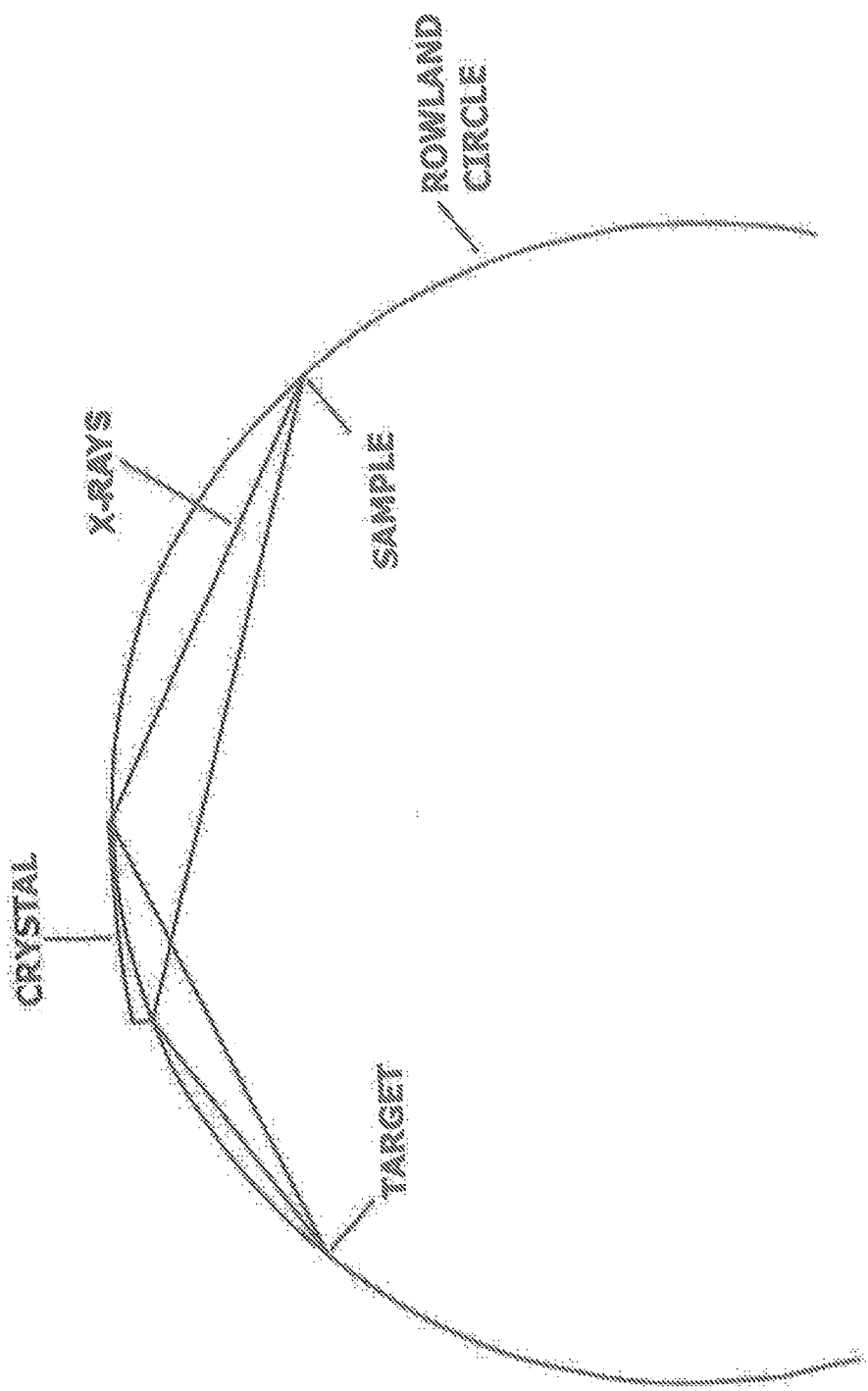

FIG. 5 shows the Rowland circle for another embodiment of the invention.

Figure 6A:
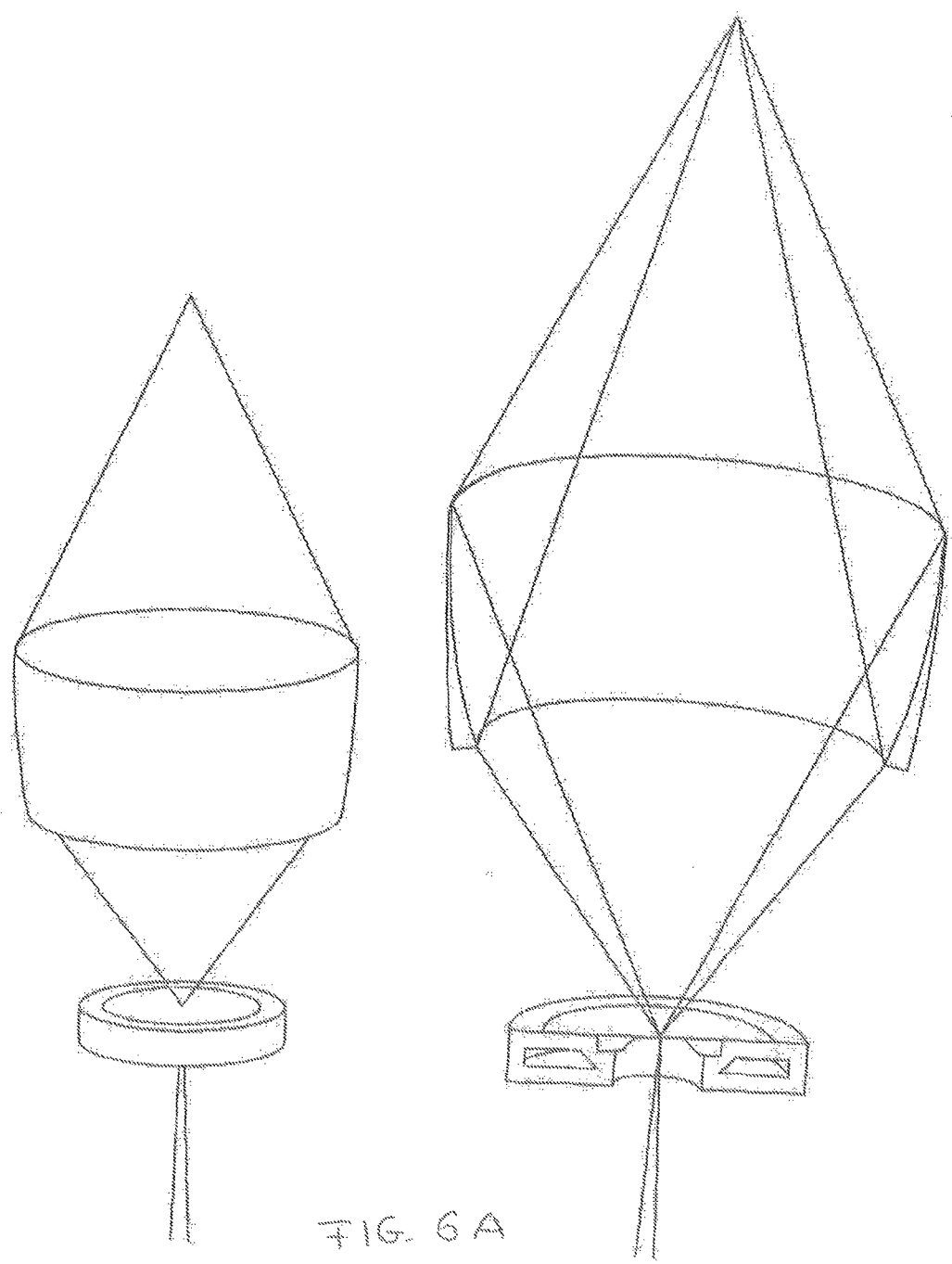

FIGS. 6A and 6B show, respectively, a perspective view and a cross-sectional schematic view.

FIGS. 7 to 10 illustrate alternative target and monochromator arrangements.

Figure 11:
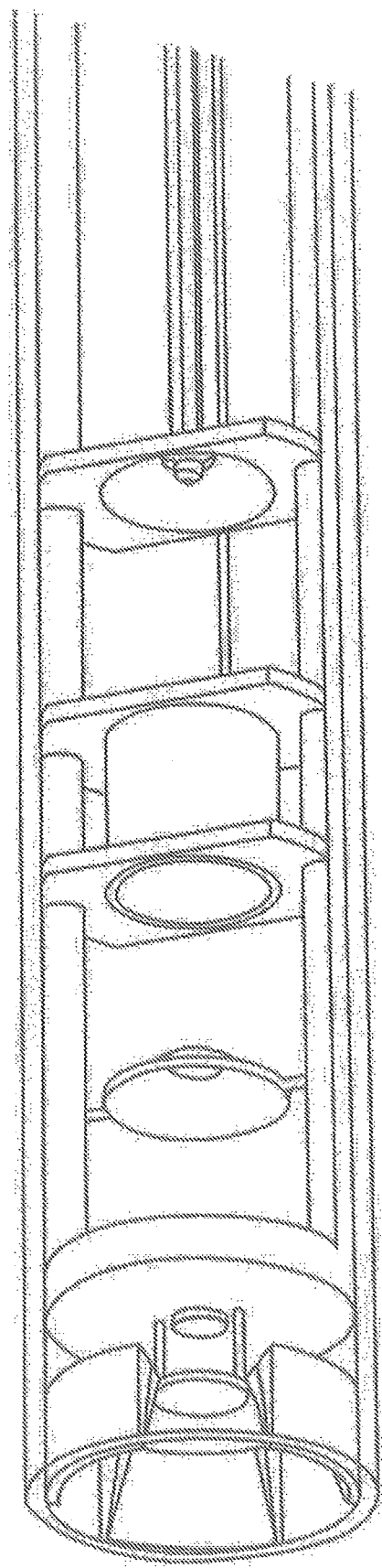

FIG. 11 shows a conceptual perspective view of how the in-line device might be laid out. The outer tubulation has been made transparent in the figure for ease of explanation only.

Figure 1:
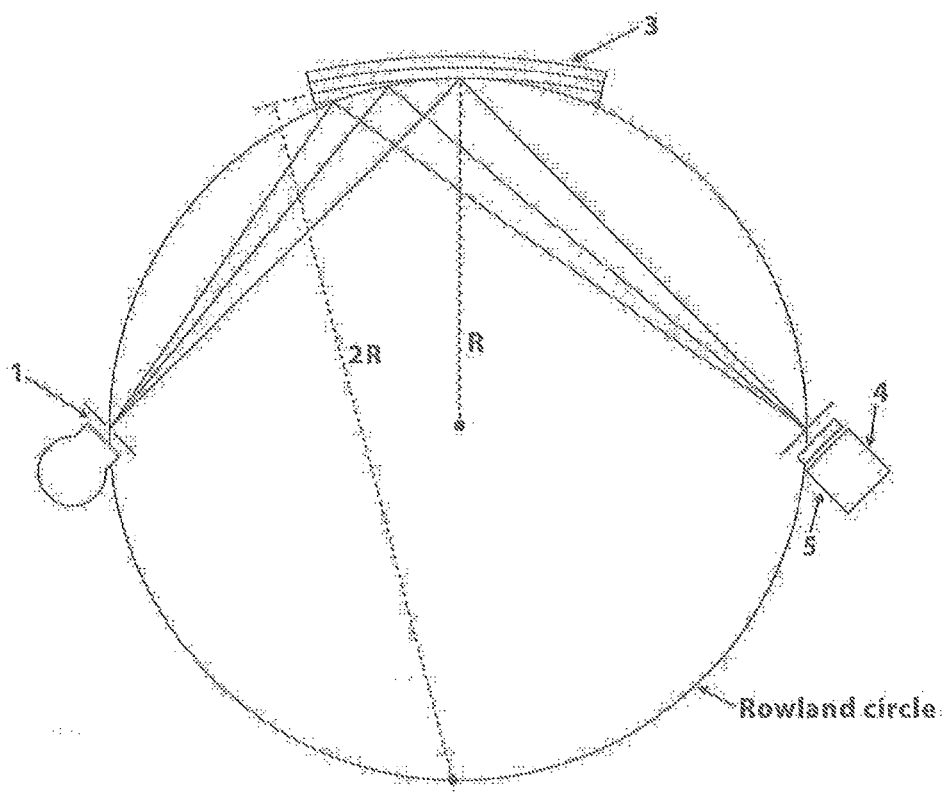
FIG. 1 is an explanatory diagram of a Rowland circle.
Figure 2:
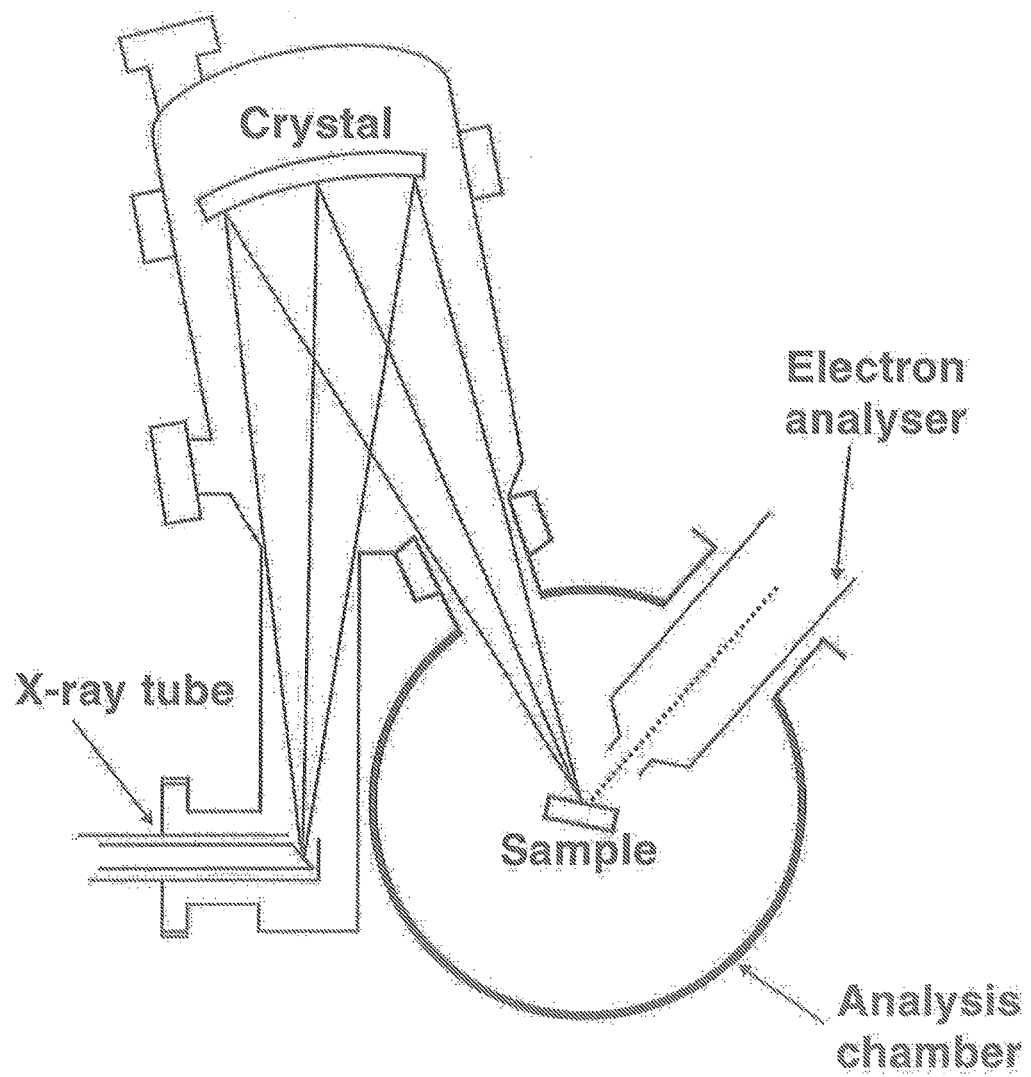
FIG. 2 is a schematic view of an existing X-ray source and analysis apparatus.
Figure 3B:
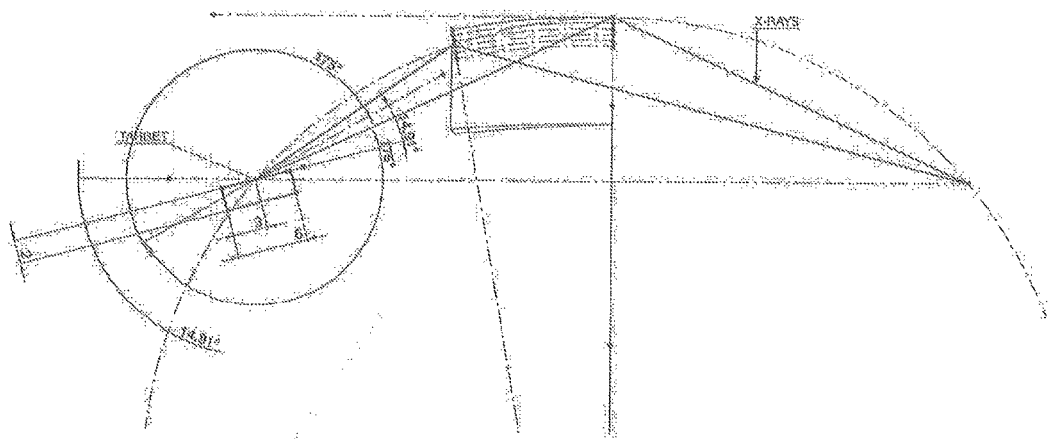

Compared to the tall configuration of the prior art systems as shown in FIG. 2, the relative arrangement of the present invention is more linear as shown in the example of FIGS. 3A and 3B.

The sample 4 to be analysed is located within a vacuum chamber 7. The vacuum chamber preferably has available a single vacuum port 8, via which instruments can be introduced into the chamber, and into which the X-ray source of the present invention can be fitted.

At the port 8 of the vacuum chamber 7, a flange 9 is preferably provided by means of which instruments including the X-ray source of the invention can be mounted to the vacuum chamber. These flanges are generally of a standard size. Accessories and instruments to be mounted to the vacuum chamber are generally provided with a mating flange of a corresponding size, so that the flange of the instrument and the flange of the vacuum chamber can be mated together and fastened, for example, by means of bolts or screws 10.

The mounting flange is the preferred embodiment, as this is present in commercially available XPS systems. It is, however, conceivable that other mounting arrangements could be provided.

The X-ray source of the present invention comprises a tubular outer housing 6, the diameter of which is preferably selected to fit within a standard vacuum port 8 of a commercially available vacuum chamber 7. Of course, different size ports are available and will be made available in the future and corresponding sizes of housings will be available.

One end 11 of the tubular housing 6 is preferably closed and the other end 12 of the tubular housing is either open or provided with a window through which the generated X-rays exit the tube and are directed towards the sample 4.

Connectors (not shown) for, e.g., water cooling and power are preferably provided on the housing near the closed end 11.

Within the tubular housing, preferably along the central axis, but this is not essential for functioning of the invention, is provided an electron gun 2 that emits electrons that strike a target 1 to cause emission of X-rays.

A target is provided, again preferably with the point at which the electrons are intended to strike the surface of the target, being arranged along the same axis as the electron gun, and preferably, but not exclusively, the central axis of the housing.

In preferred arrangements, a monochromating crystal 3 is then provided between the target and the downstream end 12 of the housing 6, with the crystal 3 being of such a material and configured and shaped and positioned such that X-rays emitted from the surface of the target 1 are diffracted by the crystal 3 onto the sample 4. In other examples, described more below, the crystal may be upstream of the target.

In the preferred arrangement, the electron gun 2, the point at which the electrons strike the target 1, and the focal point of the X-rays from the crystal, on the sample 4, all lie along the same longitudinal line relative to the central axis of the tubular housing 6, and preferably along the central axis or parallel thereto.

The outer diameter of the tubular housing 6 is preferably selected so that at least part, and preferably most of the length of the tube protrudes into the vacuum chamber 7, through the vacuum port 8. One standard port size commonly used is a 35 mm diameter port and the flange may be a standard CF38 vacuum flange. CF38 flanges provide an external mating surface of approximately 70 mm and an internal diameter of approximately 35 mm. Other sizes can, of course, be used. Other industry standards include, for example, the CF70 and CF100 flanges.

The electron gun 2 emits electrons to bombard the target material. Any suitable electron gun may be used. In the embodiment shown in FIG. 3A, there is provided a cathode 13 and an electron steering lens arrangement 14 to guide the electrons to the target. Although not shown in detail, electrical power will be provided to the electron gun, e.g. via connectors provided on the housing. In commonly available systems, a first electrical supply comprises a DC circuit providing power to heat the cathode via two electrical connectors. The cathode heating circuit is floating (not connected to ground), the entire circuit being biased to maintain a potential difference between the cathode and the target, the target being grounded through the housing of the apparatus, so as to accelerate electrons emitted at the cathode towards the target, which is in effect an anode. In other systems, the cathode may be at ground and the target at positive potential. The size of the potential difference can be selected so that electrons arrive at the target with a particular energy. A second electrical supply is arranged to maintain a first electron lens, often referred to as a control grid, at a potential relative to the cathode via another of the electrical connectors, so as to provide an electrostatic field that can be used to control the electron current from the cathode. A third electrical supply, via a fourth electrical connector, is arranged to maintain a second electron lens at a potential relative to ground for focusing electrons travelling from the cathode to the target onto an area of the target.

The target is made of a material that produces X-rays when struck by electrons having the appropriate energy.

The target is typically a metallic coating of several micrometers thickness on a copper anode assembly. In one example, aluminium is used for the coating. In an embodiment, the region of the target that bears the electron impact may be coated onto diamond, which conducts heat better than copper. In one embodiment, the target comprises an aluminium-coated piece of CVD diamond acting as a heat spreader brazed onto a metal target body.

The target (anode) assembly may be water cooled.

In the embodiment of FIG. 3A, the target 1 is oriented with respect to the electron gun 2 and monochromator 3 such that electrons arrive at the target on the surface on which the aluminium is provided. X-rays emitted by the target that leave the target via this same surface within a particular solid angle arrive at monochromator. The angle between the direction along which the electrons arrive at the target and the solid angle is obtuse, and the target may be referred to as being in a "grazing" configuration. Whilst such a configuration is relatively easy to achieve and to cool, it does limit the angular range of the crystal, to the crystal forming an arch around ca. 140° of the housing inner surface.

In other configurations, X-rays may be radiated from a so-called transmitting target, where electrons strike a target material on the upstream side of the target and the resultant X-rays pass through the target to the monochromator crystal, or where electrons pass through the target to a target material on the downstream side of the target from which the X-rays are radiated. A so-called "folded approach" is also known, where the target material is on the upstream side of the target such that the X-rays radiate back upstream to a monochromator crystal that focuses them downstream. Such configurations might allow the possibility of an annular monochromator crystal, maximising the solid angle capture of X-rays. Examples will be described in more detail below.

X-rays are generated from the target material in all directions. A proportion of these will arrive at the monochromating crystal, where the X-rays of a selected wavelength or a narrow wavelength band of interest is focused onto the sample for analysis. The solid angle that the collecting face of the crystal subtends at the target is approximately proportional to the X-ray flux delivered at the sample.

The monochromator 3 may comprise a material that selectively diffracts the X-rays according to Bragg's law to achieve the focusing. The material may be selected according to the geometry of the apparatus. A suitable material may be a mica, such as muscovite or paragonite, or other crystalline silicates such a rankinite, ferrocarpholite, walstromite or liebauite. These materials generally have Bragg angles for Kα X-rays radiated by an Aluminium target, that are low enough to facilitate a geometry that allows the monochromator to be sufficiently small.

In one example, the monochromator 3 comprises a crystalline material having a Bragg angle for the X-rays of the selected wavelength that is no more than 45°. It is particularly preferred that the Bragg angle for the X-rays of the selected wavelength is no more than 40°.

Whichever configuration is used, there are special constraints that apply to the Rowland circle geometry, in the most preferred embodiments of the invention.

The target 1, crystal(s) 3 and focal point should preferably all lie within the envelope of a tube of diameter arranged to fit in the port of a vacuum chamber containing a sample. One commonly available port size is 35 mm and the tube diameter would then be slightly less than 35 mm, e.g. 33 mm or 34 mm, as per standard tubing used with, for example, CF38 vacuum flanges (a "CF38" flange has a 70 mm or 2¾ outside diameter). A similar size flange may also be identified as a DN40 flange. Various naming conventions are used to identify vacuum flanges.

The target and focal point should preferably lie along the centreline of this diameter, as XPS systems are usually designed to work this way. The advantages of the in-line arrangement can, however, still be obtained with the apparatus off-centre relative to the vacuum port 8 to which it is attached to the chamber 7.

It is important commercially that the in-line X-ray source can be retro-fitted to existing XPS systems. Whilst described for use with a standard CF38 flange, consideration is also being given to making a prototype for a CF100 flange (to fit within a diameter of around 95 mm) for easier manufacture—both CF38 and CF100 port sizes are commonly found on vacuum chambers. Other known flanges are the CF50, CF64 and CF70. The inventive concept can be applied for use with any size flange. Almost invariably, many of the ports of a vacuum chamber share a common focal point within the chamber; in XPS this focal point is the sample. This is why the target and focal point are preferably along the centreline of the tube.

It is not essential that the whole of the Rowland circle is contained within the tube diameter, neither does it need to share a centreline with the tube, as long as the requirements for the target, crystal and focal point are met.

Figure 3C:
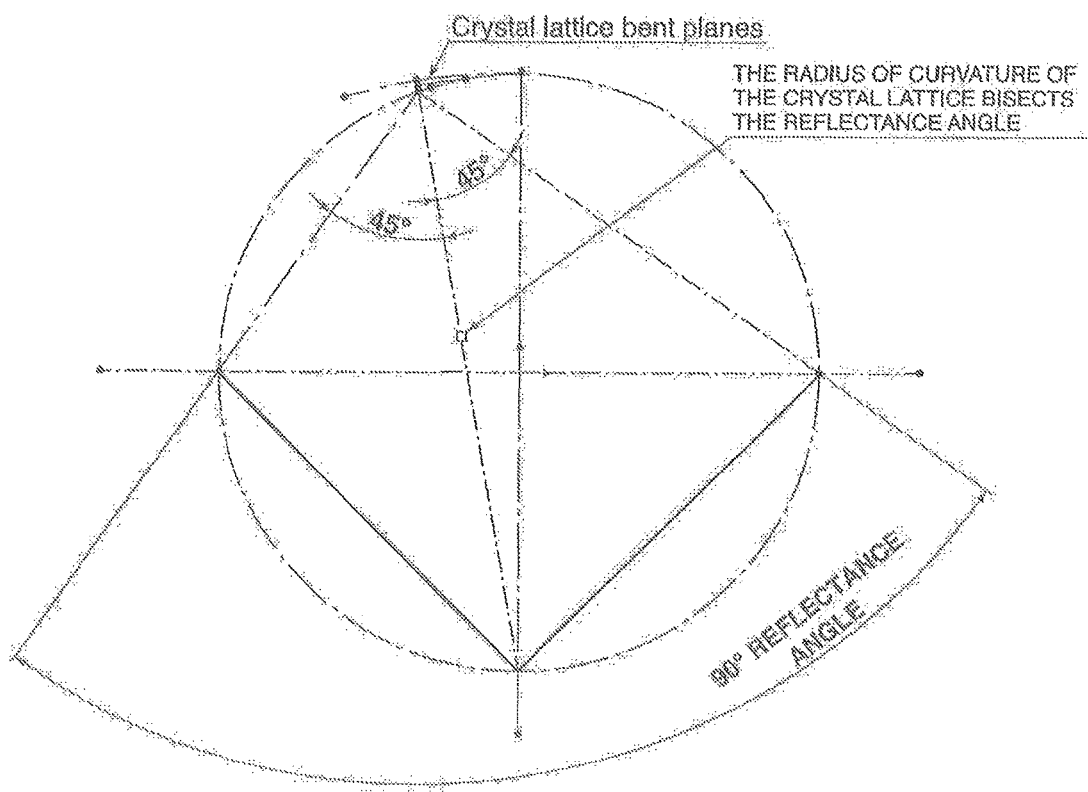

If we imagine the centreline of the tube to be horizontal, with the crystal positioned vertically above it, and that the crystal in the Johansson geometry is repositioned around the Rowland circle towards the source, the lattice layers become inclined relative to the horizontal: their left hand side is lower and their right is higher. This causes two things to happen, as illustrated in FIG. 3C.

X-ray photons from the source no longer strike the lattice layers at an angle of 45°; the angle will be smaller. Therefore, according to Bragg's law, the X-rays of the desired wavelength will no longer be focussed, by a crystal with a given lattice spacing, onto the sample.

The focal point for the desired wavelength will follow the crystal the same distance around the Rowland circle; it will no longer be horizontally opposite the source.

If we wish to position the crystal away from 12 o'clock on the Rowland circle, we should think in terms of extending the crystal rather than moving it. The crystal can be extended towards the target, and the unwanted portion of the crystal can be removed. This way, the centre of curvature of the crystal planes remain centred on the lowest point of the Rowland circle and the target and focal point remain opposite each other.

This works because of a simple rule of geometry: any two angles subtended at the diameter by a chord and on the same side of the chord are equal. Each identical half of the reflectance angle is subtended by an identical chord. These chords are identical because our focal point and target are horizontally opposite each other—or complementary. The angle will be bisected even if the target and focal point are not on the centreline of the circle, as long as they remain complementary.

Reflection effectively occurs from a series of imaginary tangents to the crystal lattice planes where the lattice planes meet the Rowland circle. The bisected reflectance angle is a requirement of Bragg reflection: identical incident and reflected angles, as for a normal mirror.

By keeping the lattice curvature centred at the 6 o'clock point, and keeping the target and focal point complementary, we can place the crystal(s) and target in different positions relative to each other to best meet design needs (e.g. longer working distance).

There are, of course, manufacturing constraints to consider. For example, for any given Rowland circle, moving the crystal position away from the topmost point will increase the curvature of the lattice layers as the crystal is closer to the 6 o'clock position (shorter radius of curvature). The lattice layers will also intersect the Rowland circle at a steeper angle. Manufacturing constraints will also affect the size of crystal: for maximum photon harvesting the crystal could extend over much of one hemisphere of the Rowland circle, but this would present difficulties in bending and bonding the crystal to its substrate.

In addition to the bend in the crystal planes to meet the extended Johansson geometry, the crystal has a second curvature. This follows the inner surface of the tube housing. The crystal footprint formed by bending and grinding the crystal to the Johansson geometry is rotated about an imaginary line joining the target and the focal point such that a hoop is formed in and out of the plane of the page. The Rowland circle and associated geometry rotates along with the crystal. While this bend is more severe than the initial diffracting bend, it opens up the full 360° sweep of the rotational symmetry of the device for the harvesting of X-rays. Producing a crystal with a full 360° sweep is considered unfeasible; a more likely solution is a number of crystal segments positioned around the outside of the device.

It is preferred that a surface of the monochromator upon which the X-rays being focused are incident subtends more than 90°, including any gap in the surface, in a direction or directions broadly circumferential to the long axis of the housing. It is particularly preferred that the surface subtends 360°, e.g. that the monochromator is substantially ring-shaped. This increases the solid angle of X-rays incident upon the monochromator. Hence, the proportion of X-rays radiated from the target that are focused on the sample may be increased, thereby increasing the efficiency of the apparatus.

Various design options have been considered for the present invention and some of these are discussed below. The various options for the in-line design are based on the same geometry, as discussed earlier. The Bragg angle used in the design depends on the crystal material chosen and the way it is cut to expose the lattice planes.

In practice, it can be difficult to bend a crystal to the required radius. One idea is that the substrate is stepped to approximate the required bend in the atomic layers, and thin sections of crystal are applied to these steps, allowing much thinner (easier to bend) crystal pieces to be used. There might be some subsequent shaping of the steps to closer approximate the top geometry.

Example 1—In-Line Geometry Using Beryl Bragg Crystal

Figure 4A:
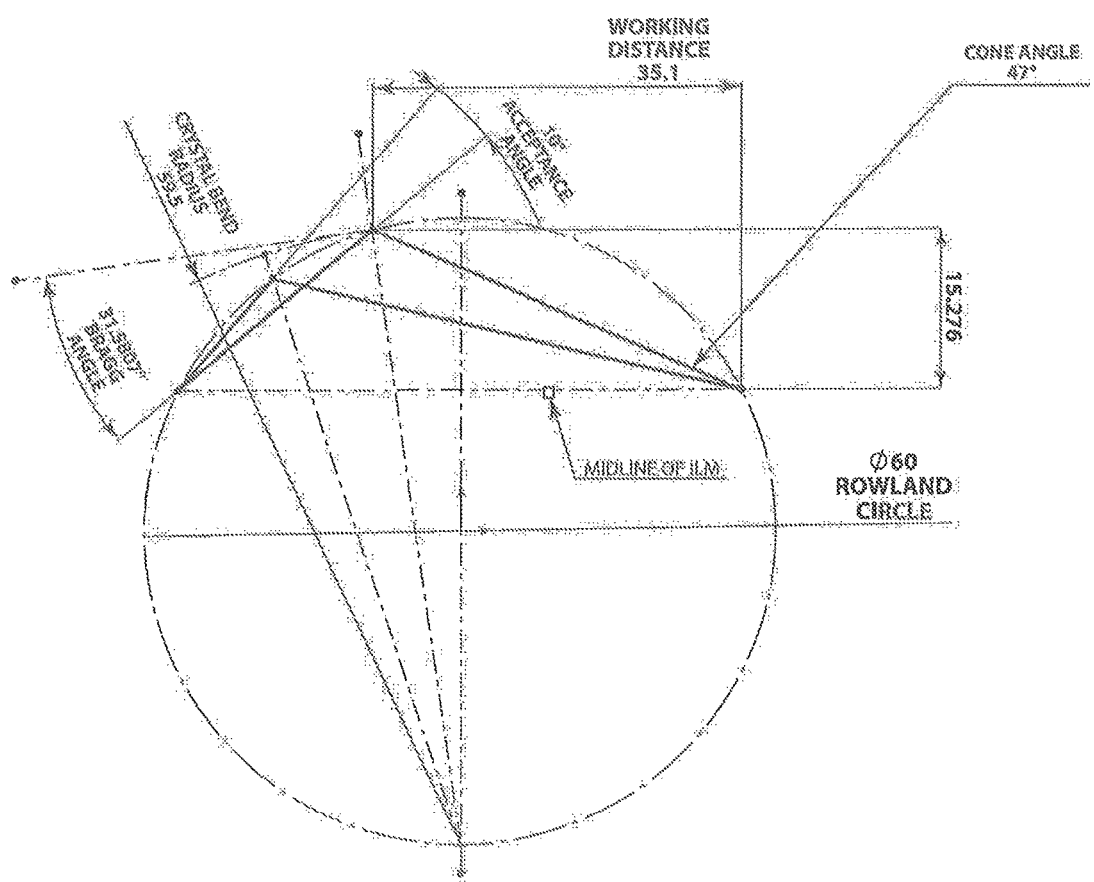
Figure 4B:
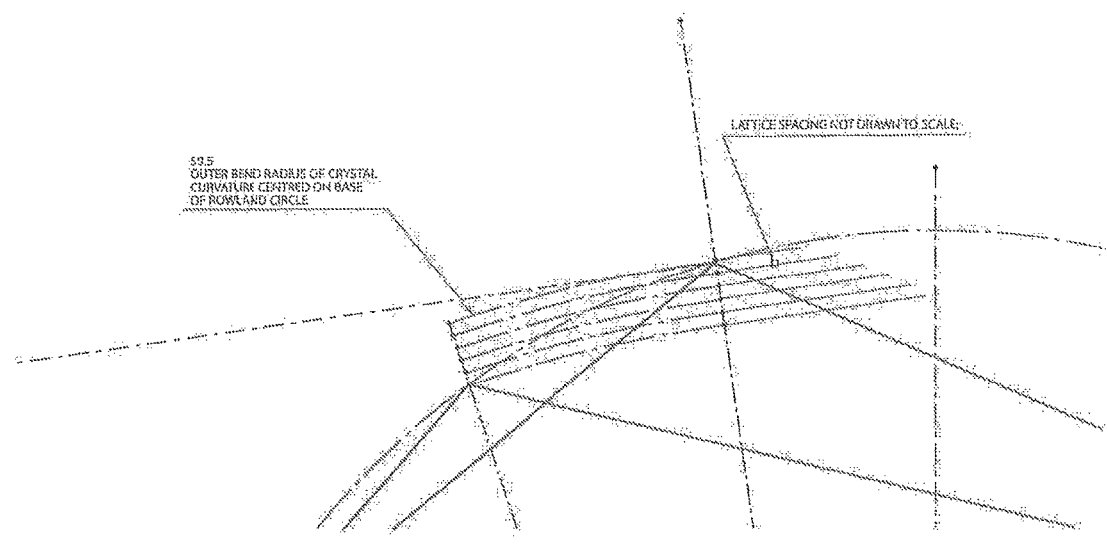

The principle of the invention is well-illustrated by the design shown in FIGS. 4A and 4B, using beryl crystal, a beryllium aluminosilicate mineral.

The important parameters available for adjustment in design optimization are:

Acceptance angle—the solid angle of X-ray capture can be increased by covering a larger segment of the Rowland circle with the crystal Crystal position—working distance can be increased by having the crystal closer to the target, but the captured angle will be reduced if the crystal stays the same size Rowland circle—the working distance can be increased by using a larger Rowland circle, but this will result in a shallower Bragg angle, requiring a change in the crystal material The shallow Bragg angle provided by beryl allows a reasonable working distance by use of a large Rowland circle.

The bend of the crystal lattice layers in relation to the Rowland circle can be seen in the detail of FIG. 4B:

The solid crystal is a sweep of this footprint rotated around the midline of the device. The outer surface of the crystal is located at or very near the inside of the tube housing, with, in this example, nominal internal diameter 33 mm. The 3D nature of the crystal in relation to the Rowland circle and the curvature of the lattice is shown in FIG. 4C.

Figure 4C:
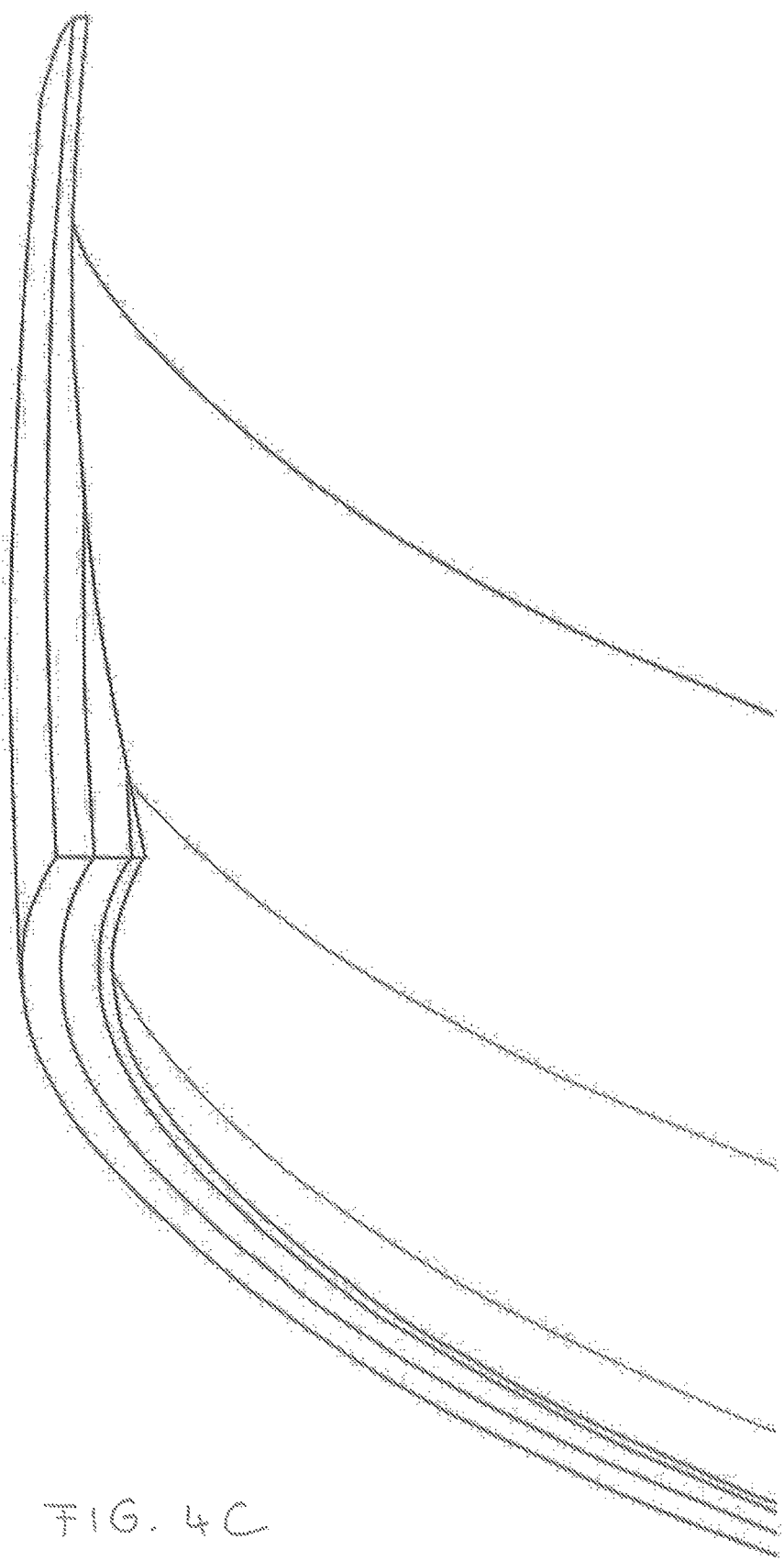
Figure 4D:
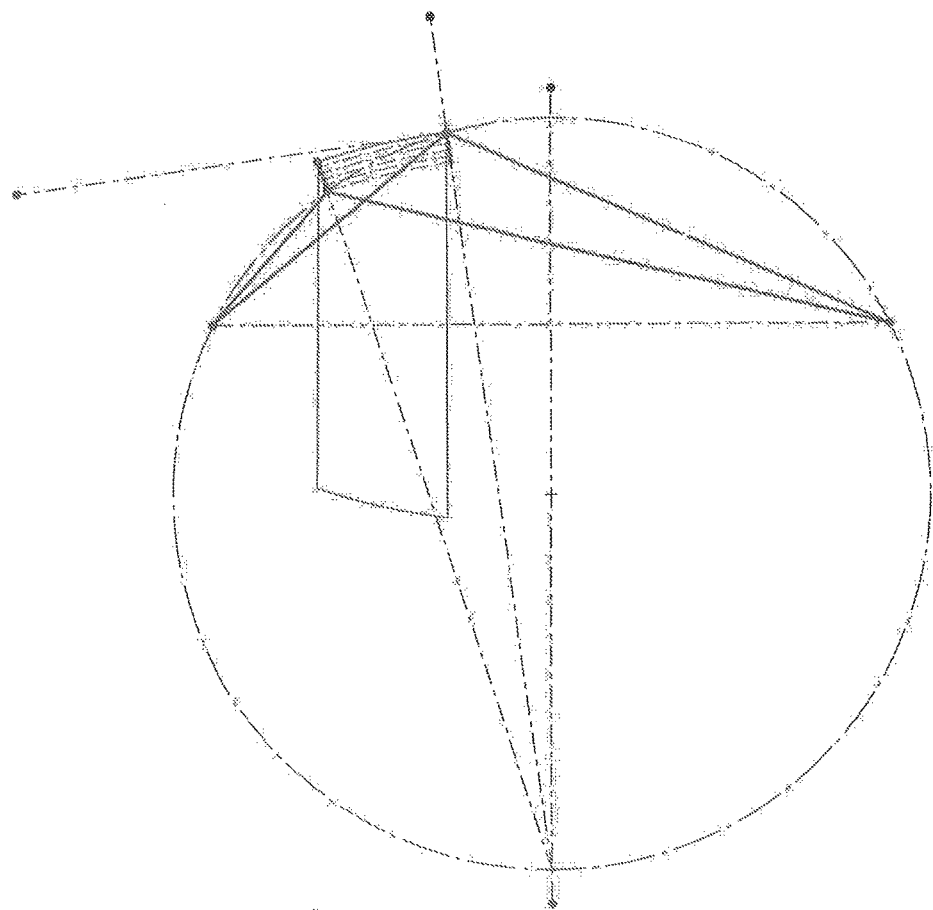

In principle, the full 360° of sweep is available for X-ray capture as shown in FIG. 4C, showing a side view of a hypothetical wedding-ring-shaped crystal).

In reality, the crystal is likely to consist of a number of segments, each bound to a substrate, using a large proportion of the 360° sweep.

Example 2—In-Line Geometry Using Muscovite Bragg Crystal

Muscovite is a mica mineral, and the characteristic layered structure gives it good flexibility. It is inexpensive, proven in vacuum systems and can be synthesized. The Bragg angle is shallower than for beryl, so in this design the crystal remains near 12 o'clock to maximise solid angle of capture, whilst maintaining a reasonable working distance.

In this design as shown in FIG. 5, the solid angle captured is 0.54 steradians, or 4.3% of a full sphere.

Of course other monochromator crystals can be used according to design requirements.

The target must be configured and arranged to generate X-rays when bombarded with electrons from the electron gun. Various types and positioning of targets are known. Some have been found by the inventors to have particular advantages in the "in-line" geometry of the invention.

In the original design concept for the in-line device of the invention, it was envisaged that either electrons from the gun or the generated X-rays should pass through the substrate, e.g. diamond part of the target. An alternative system, using a target laid back at a shallow angle, may also be an option.

In the images shown in FIG. 6A and in cross-section in FIG. 6B, showing a possible configuration of a "transmission target" in which electrons are passed through the target and the X-rays are generated by the target material on the downstream side of the target. In one example, the electrons pass through the diamond (or other selected substance), the focussed beam of electrons from the left impinges on a thin section of diamond in the centre of a water cooled copper disc. On the downstream (right) face of the disc is the thin film of aluminium target material that generates the X-rays. The captured and focussed X-rays are represented in grey.

There is some signal loss at the transmission stage, but there are advantages to this configuration. Most of the heat is delivered into the thin diamond section rather than directly onto the aluminium (or other target material), so this might assist with heat dissipation. The electrons have a lower average energy after transmission, so the aluminium film could be thinner; this is easier to manufacture and minimizes X-ray attenuation.

Figure 7:
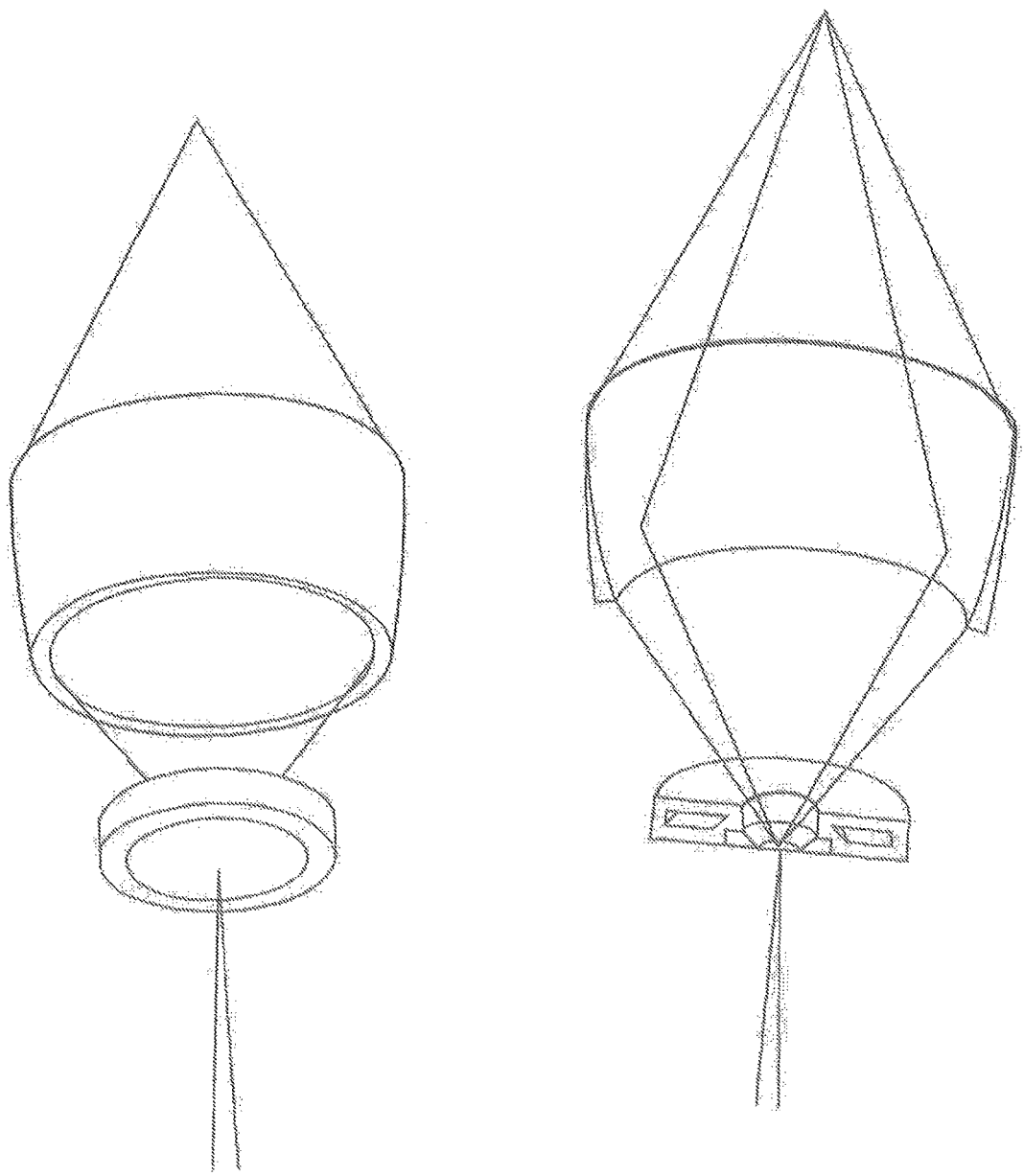

In an alternative configuration shown in FIG. 7, X-rays are transmitted through the target. The electrons would strike the target material, e.g. aluminium film, on the upstream side of the target and the X-rays would pass through the target, e.g. diamond. The advantage of this system is that X-rays transmit more efficiently through diamond than do electrons. This may allow use of a lower energy electron beam to help preserve the aluminium, which in this configuration receives the electrons directly.

Figure 8:
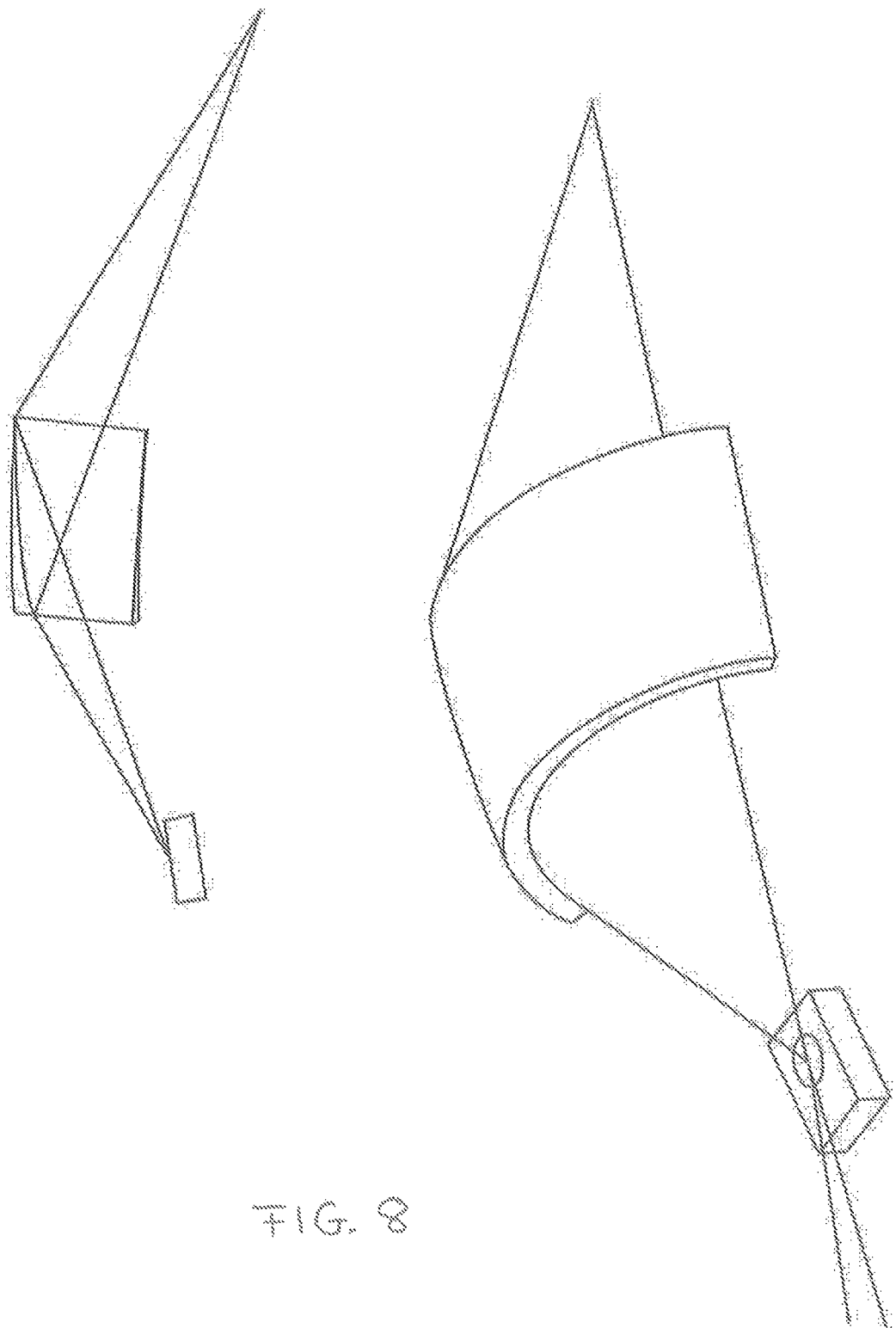

In an alternative embodiment, shown in FIG. 8, the electron beam strikes an inclined target at a shallow angle. There is no transmission of X-rays or electrons through the target—the electrons strike the target and X-rays are radiated close to where the electrons strike. Whilst such a configuration is simpler than for transmission targets, the full 360° sweep (i.e. an annular crystal) is unavailable if a planar target is used. Otherwise, the geometry is identical.

The solid angle captured in this design is lower, approximately 0.21 (1.7%) The shallow angle means that the small area where the electrons strike the target is smeared out somewhat, which should make cooling less of an issue. The corresponding shallow angle of the line-of-sight from the Bragg crystal should mean that a small-spot focal point is still possible at the sample. Put another way, the crystal 'sees' the smeared-out spot at such a shallow angle that it appears unsmeared.

Figure 9:
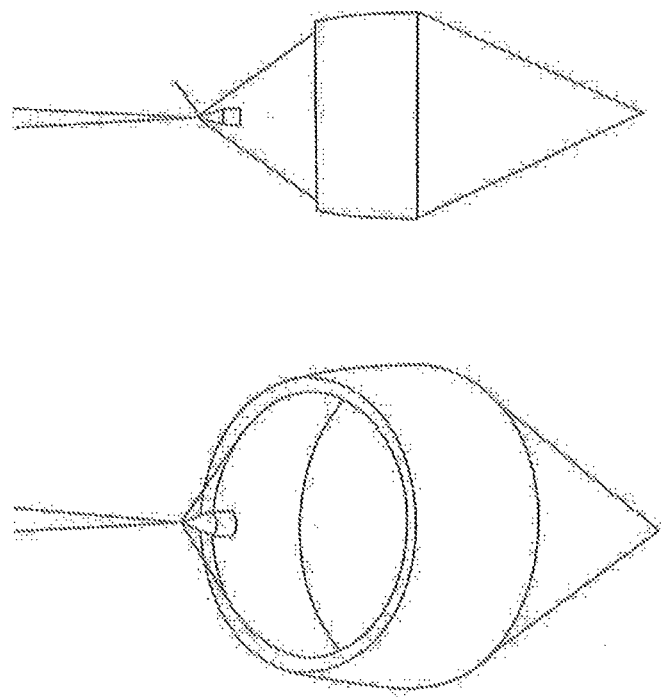

Using a non-planar target as shown in FIG. 9 may allow utilization of, nominally, the full 360° sweep. The target surface would be rolled round into a sharp pencil point shape. This would be challenging to manufacture and, possibly, to cool, although the focussed electron beam would be even further smeared out on the target than with the planar target.

Figure 10A:
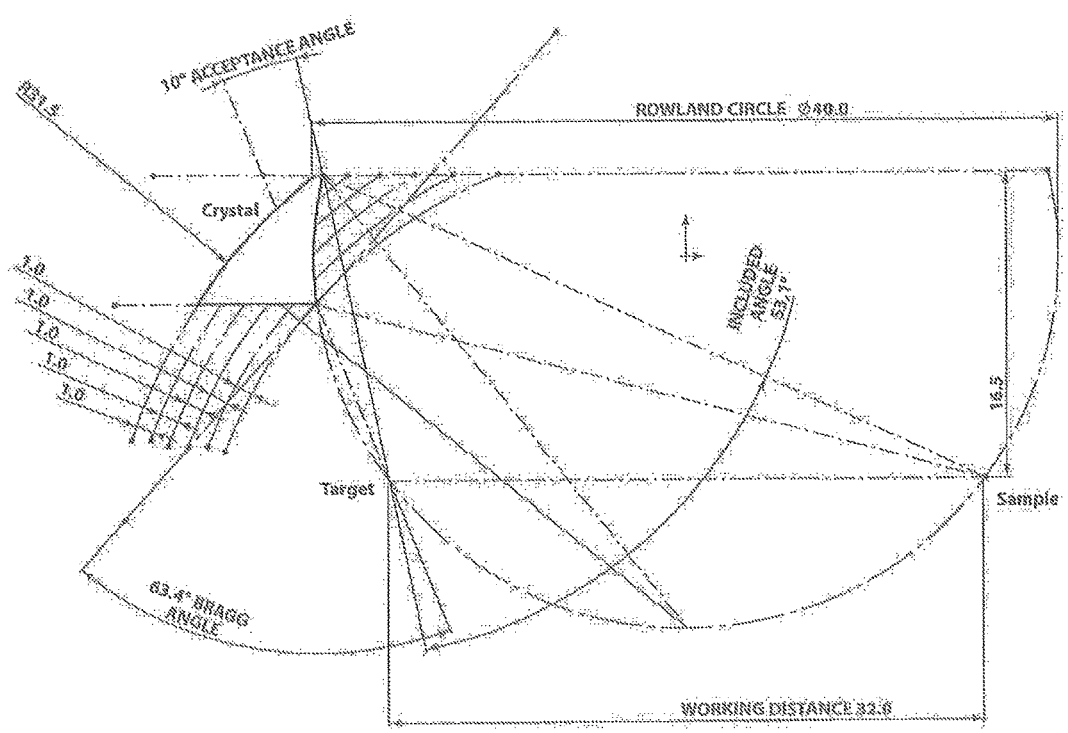

There is another possible adaptation of the target geometry in which the captured X-rays are travelling back upstream before being focussed forwards onto the sample. This has become known as the folded approach, although from the point of view of the user this is still an in-line configuration. The same principles of the crystal geometry and the Rowland circle apply as before, but in this configuration the target is on the underside part of the Rowland circle, while the crystal is close to halfway down, as shown in FIG. 10A. A cross-sectioned view of such an embodiment is shown in FIG. 10B.

This configuration has the advantage of being a non-transmitting target and having, nominally, the full 360° sweep available.

The thickness and bend in the crystal are quite extreme in the design of FIG. 10. There does not appear to be much flexibility in the design parameters, so the Bragg angle is likely to remain close to 63.4°. The nominal working distance is 32 mm, but a portion of the anode assembly (that carries the target) will protrude beyond that, so 30 mm would be a reasonable expectation.

Mica minerals such as paragonite or rankinite have suitable lattice spacings, but it is not yet clear that these occur at a useable orientation within the structure. Further investigation is required.

However the target and crystal are arranged and configured, the X-ray source of the present invention will have an essentially in-line configuration within the envelope of a tubular housing arranged to fit with a vacuum port of a commercially available vacuum chamber containing a sample for analysis. This can be seen in the example shown in FIG. 11.

The narrow wavelength band of X-rays will, due to the configuration of the target and crystal in the tubular housing, strike the sample in the vacuum chamber at the focal point that is also within the envelope of the housing, and the sample can be analysed in a known manner using a detector or analyser 5.

The In-line monochromated X-ray source of the present invention will preferably retro-fit onto existing XPS systems but will be considerably more compact and less expensive than the current arrangements. It has the potential to exceed the performance of existing systems in terms of X-ray flux and the size of the focussed X-ray spot.

The invention claimed is:

1. An X-ray source comprising:
   an elongate tubular housing adapted to be fitted into a port of and extend into a vacuum chamber containing a sample to be analysed, said housing containing:
   an electron gun and a target mounted in the housing, the electron gun being arranged to direct electrons to a point on the target such that the target radiates X-rays; and
   a monochromator arranged to focus X-rays radiated from the target to a focal point on a sample in the chamber;
   wherein the tubular housing has an inner diameter (D) and a central axis along its length, and wherein the monochromator is positioned, and comprises a material selected such that the focal point of the X-rays on the sample lies at a radial distance from the central axis not greater than the radius (D/2) of the housing, and wherein the point on the target is also at a radial distance from the central axis not greater than the radius of the housing, such that the target, the monochromator and the focal point on the sample are all contained within a radial area not greater than the diameter of the housing.

2. The X-ray source of claim 1, wherein the tubular housing is adapted to be fitted to, and extend through, a port of the chamber.

3. The X-ray source of claim 2, wherein the tubular housing is adapted to be fitted to the port by means of a flange provided around the port.

4. The X-ray source of any preceding claim, wherein the tubular housing has a central axis along its length, and wherein the point on the target is positioned on the central axis, and wherein the monochromator is positioned and comprises a material selected such that the focal point of the X-rays on the sample also lies on the central axis.

5. The X-ray source of claim 1, wherein the tubular housing has an outside diameter of less than 35 mm.

6. The X-ray source of claim 1, wherein the target is a planar target arranged with a surface to receive electrons from the electron gun and to radiate X-rays towards the monochromator.

7. The X-ray source of claim 1, wherein the target is arranged to receive electrons at a first surface and to radiate X-rays from a second, opposite surface, where either the electrons or the X-rays pass through the body of the target from the first surface to the second surface.

8. The X-ray source of claim 1, wherein the target is located downstream of the monochromator and arranged to radiate X-rays back upstream to the monochromator.

9. The X-ray source of claim 1, wherein the monochromator is a diffracting crystal.

10. The X-ray source of claim 9, wherein the monochromator is a Bragg crystal.

11. The X-ray source of claim 9, wherein the crystal is not quartz.

12. The X-ray source of claim 9, wherein the crystal is provided on or close to the inner surface of the tubular housing, extending at least part way around the inner surface.

13. The X-ray source of claim 12, wherein the crystal, either as a single piece or as a series of segments and spaces between segments extends substantially right around, i.e. 360°, the inner surface of the housing.

* * * * *